(12) United States Patent
Mokelke et al.

(10) Patent No.: US 8,340,761 B2
(45) Date of Patent: Dec. 25, 2012

(54) MYOCARDIAL INFARCTION TREATMENT SYSTEM WITH ELECTRONIC REPOSITIONING

(75) Inventors: Eric A. Mokelke, White Bear Lake, MN (US); Allan C. Shuros, St. Paul, MN (US); James A. Esler, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 175 days.

(21) Appl. No.: 12/793,206

(22) Filed: Jun. 3, 2010

(65) Prior Publication Data
US 2011/0040344 A1   Feb. 17, 2011

Related U.S. Application Data

(60) Provisional application No. 61/233,018, filed on Aug. 11, 2009.

(51) Int. Cl.
*A61N 1/368* (2006.01)
*A61N 1/372* (2006.01)

(52) U.S. Cl. ............ 607/3; 607/2; 607/9; 607/17

(58) Field of Classification Search ......... 607/3, 2, 607/9, 17
See application file for complete search history.

(56) References Cited

U.S. PATENT DOCUMENTS

| | | | |
|---|---|---|---|
| 5,203,776 A | 4/1993 | Durfee | |
| 5,876,385 A | 3/1999 | Ikari et al. | |
| 6,723,083 B2 | 4/2004 | Kiemeneij et al. | |
| 7,366,567 B2 | 4/2008 | Zhu et al. | |
| 7,908,004 B1 * | 3/2011 | Gill et al. | 607/17 |
| 8,126,549 B2 * | 2/2012 | Sigg et al. | 607/9 |
| 2004/0024425 A1 | 2/2004 | Worley et al. | |
| 2004/0133243 A1 * | 7/2004 | Santamore et al. | 607/5 |
| 2006/0241704 A1 | 10/2006 | Shuros et al. | |
| 2006/0259087 A1 | 11/2006 | Baynham et al. | |
| 2006/0259088 A1 | 11/2006 | Pastore et al. | |
| 2007/0032480 A1 | 2/2007 | O'Rourke et al. | |
| 2007/0043393 A1 * | 2/2007 | Brockway et al. | 607/4 |
| 2008/0071315 A1 | 3/2008 | Baynham et al. | |
| 2009/0270941 A1 | 10/2009 | Mokelke et al. | |
| 2009/0318943 A1 | 12/2009 | Eidenschink et al. | |
| 2009/0318993 A1 | 12/2009 | Eidenschink et al. | |

FOREIGN PATENT DOCUMENTS

| WO | WO 2008/109040 | 9/2008 |
|---|---|---|
| WO | WO 2009/131862 | 10/2009 |

OTHER PUBLICATIONS

International Search Report and Written Opinion issued in PCT/US2010/037222, mailed Jul. 16, 2010, 16 pages.
Vanagt, Ward Y. et al., "Pacing-Induced Dyssynchrony During Early Reperfusion Reduces Infarct Size", Journal of the American College of Cardiology, vol. 49, No. 17, 2007, pp. 1813-1819.

* cited by examiner

*Primary Examiner* — Niketa Patel
*Assistant Examiner* — Christopher A Flory
(74) *Attorney, Agent, or Firm* — Faegre Baker Daniels LLP

(57) ABSTRACT

Methods and devices for treating a blockage in the coronary arterial system are provided. Some blockages in the coronary arterial system restrict the blood flow to a portion of the heart, causing ischemia or infarction. Such blockages may be treated by displacing, removing and/or breaking up the blockage, which allows blood to reperfuse into the infarcted portion of the heart. Before, during, and/or after the reperfusion, cardioprotective pacing is provided to the heart. The devices have multiple electrodes in order to provide multiple locations at which the cardioprotective pacing may be delivered. The devices are adapted to deliver cardioprotective pacing to the heart via the electrode that results in a relatively high level of dyssynchrony of the heart.

8 Claims, 6 Drawing Sheets

MYOCARDIAL INFARCTION TREATMENT SYSTEM WITH ELECTRONIC REPOSITIONING

CROSS-REFERENCE TO RELATED APPLICATION

This application claims benefit under 35 U.S.C. §119 to U.S. Provisional Application No. 61/233,018, filed Aug. 11, 2009, entitled "MYOCARDIAL INFARCTION TREATMENT SYSTEM WITH ELECTRONIC REPOSITIONING," which is incorporated herein by reference in its entirety for all purposes.

BACKGROUND

Myocardial infarction (MI) is a condition in which a portion of the blood flow to the myocardium has been blocked, causing a region of the myocardial tissue to be ischemic or infarcted. For example, an embolus or blockage (e.g., a thrombus or other mass of material) may block one or more coronary arteries, causing a decrease in, or completely eliminating, blood flow to a region of the heart. The region of the heart to which blood flow has been reduced or eliminated may be referred to as the infarct zone. A variety of treatments exist for addressing MI, including various methods for deforming, capturing and/or breaking up the thrombus in the coronary arteries. There exists a need for additional devices and methods for treating MI.

SUMMARY

Some embodiments of the present invention include a method of treating a heart having a myocardial infarction where the heart includes a coronary vascular system. The method comprises introducing a portion of a MI treatment system into a patient's vasculature where the MI treatment system includes a guidewire, a guide catheter, a therapeutic device, and first and second electrodes. The guide catheter is advanced through the vasculature, accessing a portion of a coronary vascular system. The guidewire is advanced through the guide catheter, through a portion of the coronary vascular system and through a blockage in the coronary vascular system. The therapeutic device is introduced over the guidewire and to the blockage. The blockage is opened with the therapeutic device. The heart is paced first from one of the first and second electrodes, the heart is subsequently pacing from the other of the first and second electrodes, and the QRS interval is monitored while individually pacing from the first and second primary electrodes. It is determined which of the electrodes provides the widest QRS interval and the heart is paced from the electrode that provides the widest QRS interval. The pacing is provided from this electrode contemporaneously with opening the blockage with the therapeutic device.

In addition, some embodiments of the present invention include a method of treating a heart having a myocardial infarction where the heart includes a coronary vascular system with a blockage in a portion of the coronary vascular system. The method includes introducing one or more devices into the coronary vascular system, the one or more devices having a total of two or more electrodes disposed thereon. The electrodes are disposed in at least two different locations in the coronary vascular system. The heart is paced from one of the electrodes and subsequently from another of the electrodes. A physiological parameter that represents the level of synchrony of the heart is monitored when individually pacing from each of the electrodes. The target electrode that provides the highest level of dyssynchroney is determined and the heart is temporarily paced from the target electrode contemporaneously with treatment of the blockage and reperfusing blood flow to the myocardial infarction.

Other embodiments of the present invention include a system for the treatment of myocardial infarction. The system comprises an access device for facilitating access to a portion of the coronary vascular system, a therapeutic device configured to open a blockage in the coronary vascular system, a first and a second electrode, the electrodes disposed on one of the vascular access system or the therapeutic device and a controller operatively coupled to the first and second electrodes. The controller is adapted to send a first pacing signal to the first electrode and receive first physiological parameter data when sending the first pacing signal, send a second pacing signal to the second electrode and receive second physiological parameter data when sending the second pacing signal and compare the first and second physiological parameter data and sending a pacing signal to the heart via the electrode with the physiological parameter representing the highest level of dyssynchrony.

In Example 1, a method of treating a heart having a myocardial infarction, the heart including a coronary vascular system, the method comprising: introducing a portion of a MI treatment system into a patient's vasculature, the MI treatment system including a guidewire, a guide catheter, a therapeutic device, and first and second electrodes; advancing the guide catheter through the vasculature and accessing a portion of a coronary vascular system; advancing the guidewire through the guide catheter, through a portion of the coronary vascular system and through a blockage in the coronary vascular system; introducing the therapeutic device over the guidewire and to the blockage; opening the blockage with the therapeutic device; pacing the heart first from one of the first and second electrodes, subsequently pacing the heart from the other of the first and second electrodes, and monitoring the QRS interval while individually pacing from the first and second primary electrodes; determining which electrode provides the widest QRS interval; and pacing the heart from the electrode that provides the widest QRS interval contemporaneously with opening the blockage with the therapeutic device.

In Example 2, the method of Example 1, wherein one of the electrodes is disposed on a distal portion of the guidewire and one of the electrodes is disposed on a distal portion of the therapeutic device.

In Example 3, the method of any of Examples 1-2, wherein more than two electrodes are disposed on the MI treatment system and the method includes pacing from more than two electrodes, monitoring the QRS interval while pacing from each of the different electrodes, determining which electrode provides the widest QRS interval and temporarily pacing from that electrode contemporaneously with the opening of the blockage with the therapeutic device.

In Example 4, the method of any of Examples 1-3, wherein the MI treatment system further comprises a second guidewire or lead with at least one electrode disposed thereon, the method including the step of advancing the second guidewire into a portion of the patient's vasculature other than the portion of the vasculature with the blockage, pacing from two or more electrodes including the one or more electrodes of the second guidewire or lead, monitoring the QRS interval while pacing from each of the different electrodes, determining which electrode provides the widest QRS interval and temporarily pacing from that electrode contemporaneously with the opening of the blockage with the therapeutic device.

In Example 5, the method of Example 4, wherein the second guidewire or lead is advanced into the coronary sinus.

In Example 6, the method of any of Examples 1-5, wherein the temporary pacing is provided after opening the blockage.

In Example 7, the method of any of Examples 1-6, wherein the temporary pacing is provided before opening the blockage.

In Example 8, the method of any of Examples 1-7, wherein the widest QRS interval is at least 120 msec.

In Example 9, a method of treating a heart having a myocardial infarction, the heart including a coronary vascular system with a blockage in a portion of the coronary vascular system, the method including: introducing one or more devices into the coronary vascular system, the one or more devices having a total of two or more electrodes disposed thereon; disposing the electrodes in at least two different locations in the coronary vascular system; pacing the heart from one of the electrodes and subsequently from another of the electrodes; monitoring a physiological parameter that represents the level of synchrony of the heart when individually pacing from each of the electrodes; determining a target electrode that provides the highest level of dyssynchrony; and temporarily pacing from the target electrode contemporaneously with treatment of the blockage and reperfusing blood flow to the myocardial infarction.

In Example 10, the method of Example 9, wherein the one or more devices includes a guide catheter, a guidewire, and a therapeutic device for opening a blockage in a vessel.

In Example 11, the method of any of Examples 9-10, wherein one of the electrodes is disposed at a location distal of the blockage and another of the electrodes is disposed at a location proximal of the blockage.

In Example 12, the method of any of Examples 9-10, wherein at least one electrode is disposed in a vessel other than the vessel containing the blockage.

In Example 13, the method of Example 12, wherein at least one electrode is disposed in the coronary venous system.

In Example 14, the method of any of Examples 9-13, wherein the physiological parameter resulting from a pacing signal sent to the target primary electrode is a QRS interval of at least 120 msec.

In Example 15, the method of any of Examples 9-14, wherein the temporary pacing is provided after opening the blockage.

In Example 16, the method of any of Examples 9-15, wherein the physiological parameter is one of pulse pressure, systolic pressure or MAP.

In Example 17, a system for the treatment of myocardial infarction, the system comprising: an access device for facilitating access to a portion of the coronary vascular system; a therapeutic device configured to open a blockage in the coronary vascular system; a first and a second electrode, the electrodes disposed on one of the vascular access system or the therapeutic device; and a controller operatively coupled to the first and second electrodes, the controller adapted to send a first pacing signal to the first electrode and receive first physiological parameter data when sending the first pacing signal; send a second pacing signal to the second electrode and receive second physiological parameter data when sending the second pacing signal; and comparing the first and second physiological parameter data and sending a pacing signal to the heart via the electrode with the physiological parameter representing the highest level of dyssynchrony.

In Example 18, the system of Example 17, wherein the access device comprises a guide catheter and a guidewire.

In Example 19, the system of Example 18, wherein the access device further includes a second guidewire, the second guidewire adapted to facilitate access to a portion of the coronary vasculature removed from the coronary artery containing the blockage, the second guidewire having one or more electrodes disposed thereon.

In Example 20, the system of any of Examples 17-20, wherein the controller is provided in a separate structure and is electrically coupled to the therapeutic device and/or access device, establishing an electrical pathway from the controller to the electrodes.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
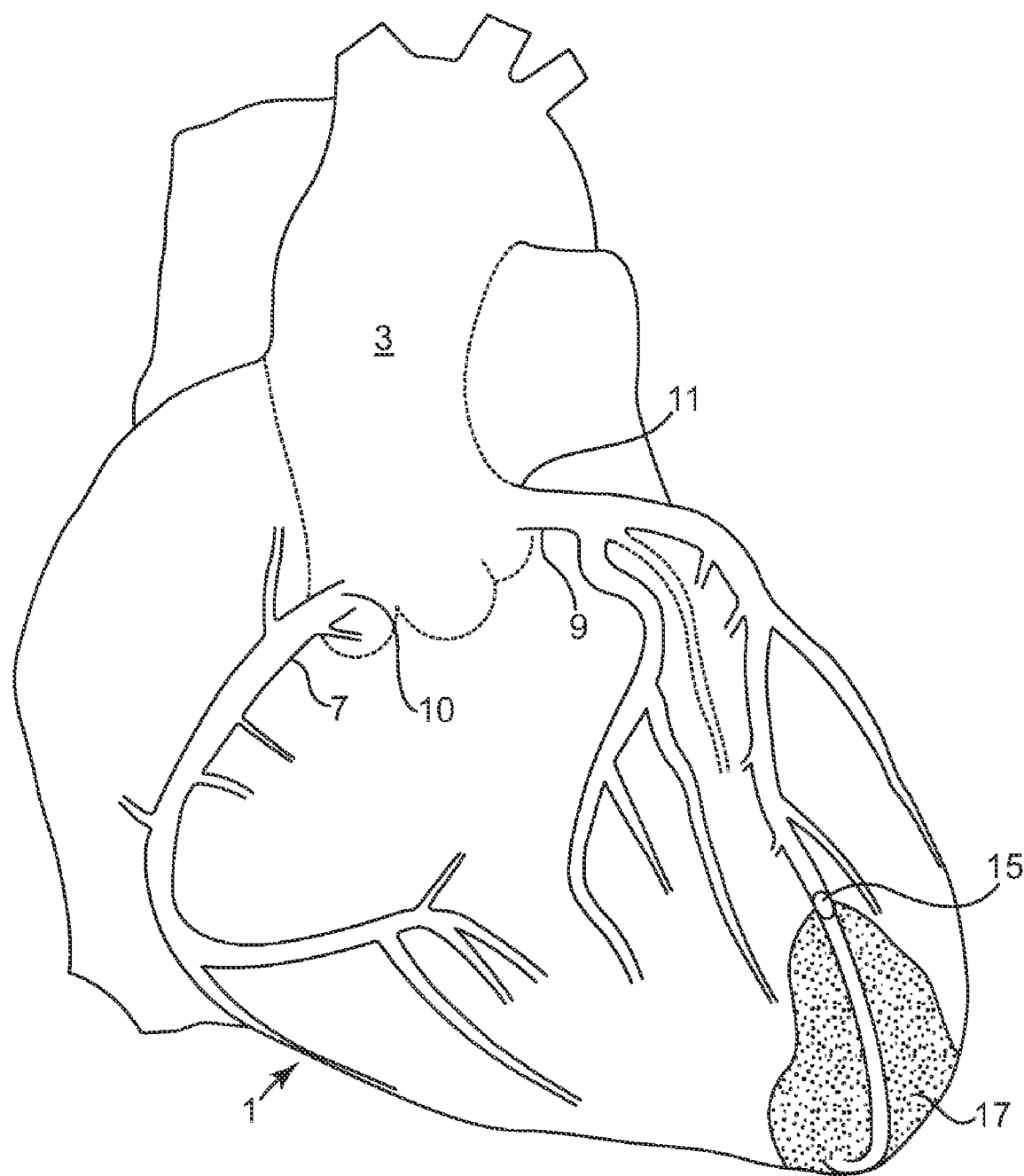
FIG. 1 shows a heart with a blockage in a portion of the coronary arteries according to some embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 shows a human heart 1 with an aorta 3 and right and left main coronary arteries 7, 9 extending from the aorta 3. Openings called ostia 10, 11 generally allow blood to flow from the aorta 3 into the coronary arteries 7, 9. Branches also form off of the main coronary arteries 7, 9 to supply oxygenated blood to the various regions of the heart. (Although many of the examples provided herein refer to the left main coronary artery 9 and its ostium 11, those of skill in the art will recognize that the methods and devices would also be applicable to the right coronary artery 7 and its ostium 10, as well as other coronary arteries and ostia that may be present in some patients.)

A blockage 15 is shown in a branch of the left coronary artery 9, although blockages are known to form in other parts of the coronary arterial system as well. The blockage 15 can be caused by an embolus (e.g., a thrombus or other materials) that becomes lodged or builds up in the artery. In some instances, the partial or complete blockage of the flow of blood through an artery causes ischemia, and possibly eventually infarction, in a portion of the heart. (In this application, ischemia and infarction of the heart may be generally referred to as a myocardial infarction). The portion of the heart 1 that is affected by the blockage 15 is indicated in the shaded area 17, and may be referred to as the infarct zone 17.

A variety of options are available for treating a MI. For example, some treatment options break up the blockage 15 so that it can flow distally through the arterial system, some treatment options displace the blockage 15, and some treatments capture and remove the blockage 15. Any of these systems may also include a filtration feature that captures portions of the blockage 15 that become entrained in the blood flow. Once the artery has been revascularized, blood flows through the artery to the affected area of the heart, resulting in reperfusion of the infarct zone 17.

It has been found that pacing the heart can in some cases have a protective effect on the portion(s) of the heart that is being reperfused. Various portions of the heart can be paced, as further discussed below. Such cardioprotective pacing is generally described, for example, in U.S. Patent Publication No. 2006/0241704 and U.S. Patent Publication No. 2006/0259087, both of which are herein incorporated by reference in their entirety for all purposes.

Cardioprotective pacing may be implemented using a number of different methods and devices. In some embodiments, a MI treatment system includes a vascular access system and a therapeutic device for opening a blockage. The vascular access system is inserted into a patient's vasculature at an access point (not shown in the figures, but the access point could be, for example, the femoral artery). The vascular access system is advanced through the vasculature and through the aorta to access the coronary arterial system. The therapeutic device may be advanced through and/or over the vascular access system and is used to open the blockage. Cardioprotective pacing is provided during the procedure, as further described in more detail below.

Figure 2:
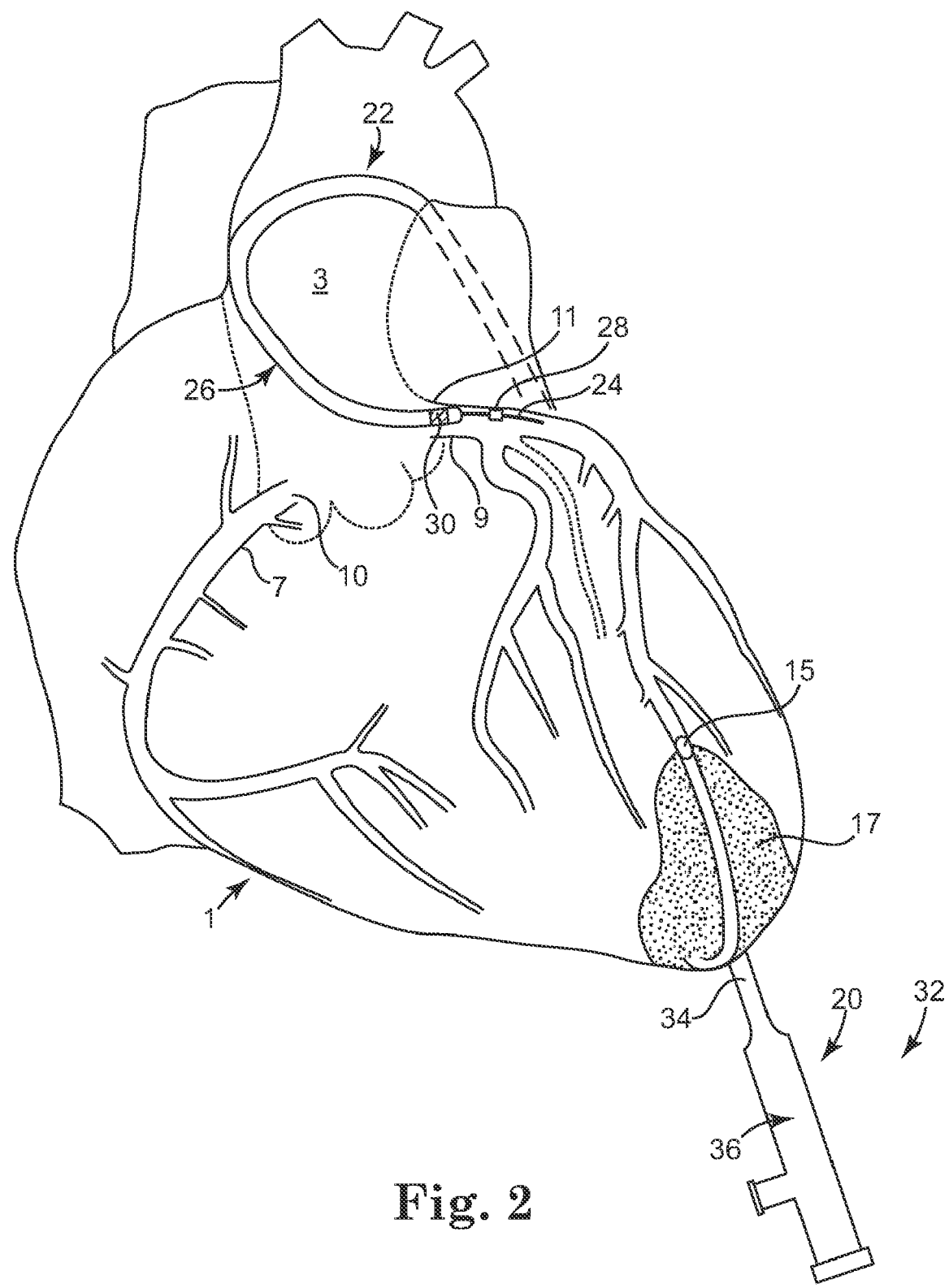
FIG. 2 shows a heart with a blockage in a portion of the coronary arteries and a vascular access system facilitating access to the heart according to some embodiments of the present invention.

As shown in the exemplary embodiment of FIG. 2, a vascular access system 20 includes both a guide catheter 22 and a guidewire 24. A distal portion of the vascular access system 20 includes a guide catheter distal portion 26. Various configurations are available for the distal portion of a vascular access system which generally facilitate access to target locations such as the coronary ostium 11. For example, in some embodiments, the guide catheter distal portion 26 may be shaped or have other features that facilitate access from the aorta into one of the coronary ostia 10, 11. For example, various catheter shapes are described in U.S. Pat. No. 5,203,776, issued on Apr. 20, 1993 to Durfee, U.S. Pat. No. 5,876,385, issued on Mar. 2, 1999 to Ikari et al. and U.S. Pat. No. 6,723,083, issued on Apr. 20, 2004 to Keimeneij, all of which are incorporated herein by reference in their entirety for all purposes. The guide catheter may also have a steerable mechanism (e.g., steering cables) that can be used to facilitate the insertion of the guide catheter into a coronary ostium.

As shown in FIG. 2, once access is provided at a target location such as the coronary ostium 11, a second portion of the vascular access system 20 such as a guidewire 24 may be advanced into the patient's vasculature. The guidewire 24 is adapted to facilitate access to branch vessels of the coronary arterial system, for example by having a canted or shaped distal portion.

The MI treatment system has multiple electrodes, for example two, three, four or five electrodes, or more than one, more than two, more than three, more than four, or more than five electrodes. As shown in FIG. 2, an electrode 28 is disposed on a distal portion of the guidewire 24 and an optional electrode 30 is disposed on or near the guide catheter distal end. The electrodes provide multiple locations at which cardioprotective pacing may be delivered. In general, as discussed in more detail below, the MI treatment system is adapted to deliver cardioprotective pacing via the electrode that results in a desired increase in the dyssynchrony of the heart. In some embodiments, this is the electrode that results in the highest level of dyssynchrony.

The level of dyssynchrony may be monitored using a number of different physiological parameters. As one example, a patient's QRS interval may be monitored, which is generally a measure of how long it takes for the ventricles to depolarize. A QRS interval wider than 120 msec implies dyssynchrony of the heart. Also, other physiological parameters are affected by the dyssynchrony of the heart, for example the pulse pressure, the systolic pressure or the MAP. Dyssynchrony generally causes these pressures to drop at least about 10 mmHg or at least about 20 mmHg.

In some embodiments, one or more electrodes of the MI treatment system may be adapted to gather data representative of a physiological parameter of the heart such as the QRS interval. Data representative of a physiological parameter includes both data that directly represents the physiological parameter as well as data that may be used to calculate the physiological parameter. These one or more electrodes may be the same electrodes that are adapted to be used for cardioprotective pacing or may be other, additional electrodes disposed on the MI treatment system. These one or more electrodes also may function together with other electrodes not on the MI treatment system to provide data representative of physiological data. For example, electrodes placed on the outer surface of the body as part of an EKG may be used alone or together with the electrodes of the MI treatment system to provide data representative of a QRS interval.

The MI treatment system also optionally includes one or more physiological sensors. As one example, an exterior blood pressure measurement device (e.g., a standard sphygmomanometer) may be used to provide data representative of MAP, pulse pressure or systolic pressure. Alternatively, a pressure sensor may be placed in a portion of the heart or the patient's vasculature to gather data representative of a physiological parameter such as MAP, pulse pressure or systolic pressure. For example, a pressure sensor may be placed in the aorta.

Electrical signals may be transmitted to and/or from the electrodes and/or sensors along conductors (not shown) disposed in the MI treatment system. Further, electrical connection may be made between the MI treatment system and a controller/power source. In this manner, an electrical pathway is established between the controller/power source and the electrodes and/or sensors. In addition, one or more of the sensors may be coupled to the controller via a wireless link. As further discussed below, the controller uses the data representative of the physiological parameter to determine which electrode to use when delivering cardioprotective pacing.

Turning again to FIG. 2, as one example of an electrical connection between the vascular access system 20 and a controller/power source, the hemostasis valve 36 is configured to make an electrical connection with the controller/power source and also is configured to make an electrical connection with the guide catheter 22 and/or the guidewire 24. For example, a portion of the hemostasis valve 36 has a connector member that makes a mechanical and electrical connection with the guide catheter, and the hemostasis valve in turn is electrically coupled to the controller/power source, providing an electrical pathway through the hemostasis valve 36, through the guide catheter 22, and to the electrode 30. Examples of such hemostasis valves are provided in U.S. patent application No. 12/422,770, entitled "Hemostasis Valve and Guidewire Pacing System", and filed Apr. 13, 2009, which is herein incorporated by reference in its entirety for all purposes.

Also, the hemostasis valve 36 has a mechanism that can be actuated to make an electrical connection with an element of the vascular access system 20 that is disposed within the hemostasis valve 36, such as the guidewire 24. The mechanism has first and second positions and, as the mechanism is actuated from the first to the second position, the mechanism makes a mechanical and electrical connection between the guidewire 24 and the hemostasis valve 36, for example by piercing an insulation layer of the guidewire 24. The hemostasis valve 36 is in turn electrically coupled to the controller/power source, providing an electrical pathway through the hemostasis valve, through the guidewire 24, and to the electrode 28. Examples of such hemostasis valves are provided in U.S. patent application No. 12/422,770, entitled "Hemostasis Valve and Guidewire Pacing System", and filed Apr. 13, 2009, which is herein incorporated by reference in its entirety for all purposes.

In other embodiments, the proximal portions of the guide catheter 22 and/or the guidewire 24 may have electrical connections that can be directly connected to a controller/power source or have electrical cables that facilitate such a connection, providing an electrical pathway for the transmission of pacing signals and/or sensed electrical signals between the electrodes and other optional sensors and the controller.

Figure 3:
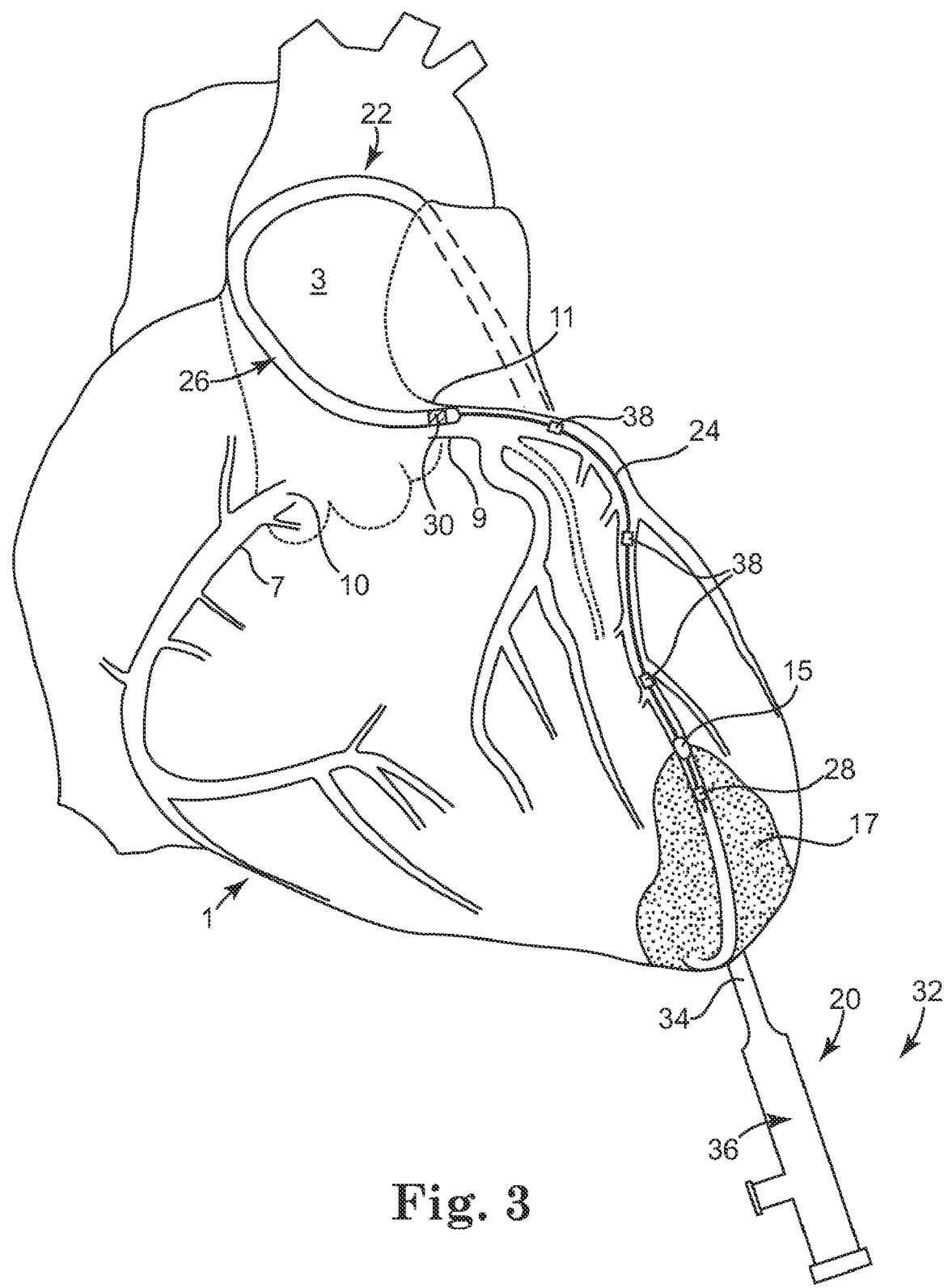
FIG. 3 shows FIG. 2 with a guidewire advanced through the coronary vasculature and through the blockage.

FIG. 3 shows the vascular access system 20 of FIG. 2 with the guidewire 24 advanced through the coronary arterial system and through the blockage 15 such that the electrode 28 is distal of the blockage 15, or in the infarct zone 17. The guidewire 24 may have a single electrode 28, or the guidewire 24 optionally has additional electrodes 38 disposed thereon for a total of two, three, four, more than one, more than two, more than three, or more than four electrodes 38 disposed along the guidewire 24. When the guidewire 24 is advanced through the blockage 15, one or more electrodes (e.g., electrodes 38) may remain proximal of the blockage 15, while one or more electrodes (e.g., electrode 28) are disposed distal of the blockage 15.

Figure 4A:
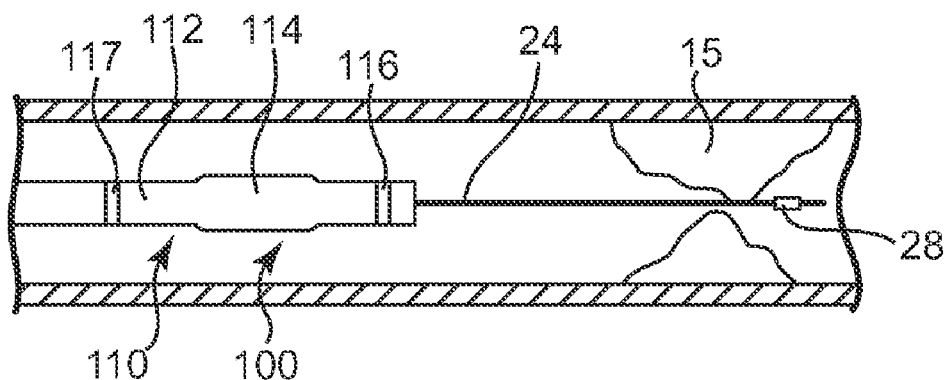
FIGS. 4A-4C show a therapeutic device that is advanced along a guidewire to treat the blockage according to some embodiments of the present invention.

FIG. 4A shows a cross-section of a vessel 100 with the blockage 15 and the guidewire 24 shown crossing the blockage 15. The guidewire 24 may have a distal portion that is sufficiently stiff to be advanced through the blockage 15. In some embodiments, the MI treatment system includes a therapeutic device 110 that is advanced along the guidewire 24 after the guidewire 24 has crossed the blockage 15. In other embodiments, the therapeutic device 110 is advanced along the guidewire 24 before the guidewire 24 has crossed the blockage 15.

Figure 4B:
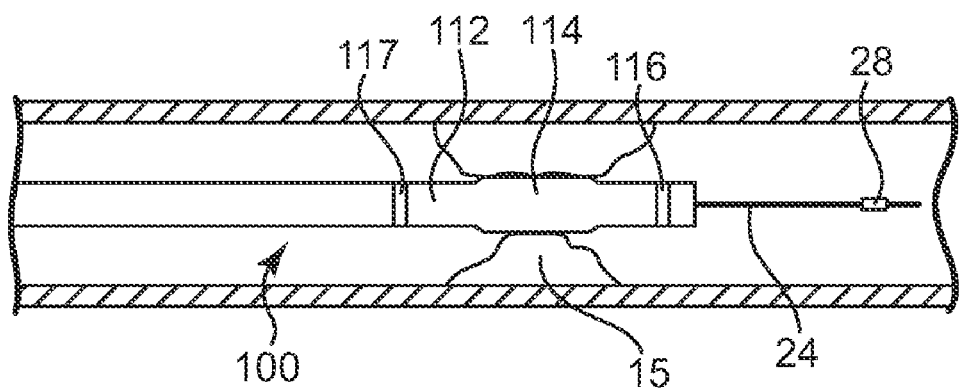
Figure 4C:
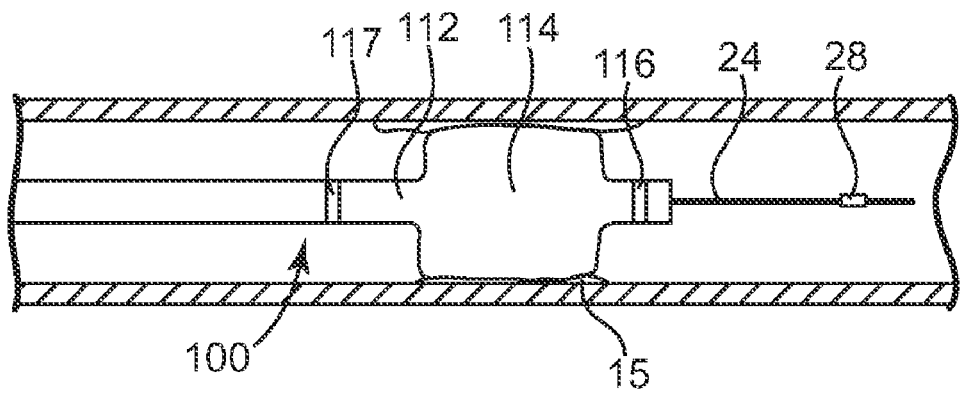

As shown in FIGS. 4A-4C, the therapeutic device 110 may be a catheter 112 with a balloon 114 disposed thereon. The balloon 114 may be selectively inflatable so that the balloon can be used to open (e.g., deform and/or break up) the blockage 15. Although the therapeutic device 110 is shown as a balloon catheter 112, other devices may be used that can facilitate the opening of the blockage 15. For example, ablation devices may be used to break up the blockage 15, stents (e.g., a stent delivered on a balloon) may be used to deform the blockage 15 and maintain patency of the vessel 100, or other therapeutic devices that open the blockage 15 may be used. In addition, portions of the blockage 15 may also be captured, for example, using a filter that can be placed downstream of the blockage 15. Such a filter may be used in conjunction with any of the devices described above to capture portions of the blockage 15 that may become entrained in the blood flow during and after the treatment of the blockage 15.

The therapeutic device 110 also optionally has one, two, three, four, more than one, more than two, more than three, or more than four electrodes 116, 117 disposed thereon. One or more electrodes 116 are disposed distal of the operative portion (e.g., the balloon 114) of the therapeutic device 110, one or more electrodes 117 are disposed proximal of the operative portion, or (as shown) one or more electrodes 116, 117 are be disposed both distal and proximal of the operative portion. Electrodes that are disposed distal of the operative portion of the therapeutic device 110 may be used to stimulate portions of the heart that are within the infarct zone 17, while electrodes that are disposed proximal of the operative portion may be used to stimulate portions of the heart that are outside the infarct zone 17.

FIG. 4B shows the therapeutic device 110 advanced into the blockage 15 such that the balloon 114 or other operative portion of the therapeutic device 110 is disposed in the blockage 15. A distal electrode 116 is disposed distal of the blockage 15, or within the infarct zone 17 and a proximal electrode 117 is disposed proximal of the blockage 15. As shown in FIG. 4C, the balloon 114 or other operative portion of the therapeutic device 110 may be used to open the blockage 15. The balloon 114 in FIG. 4C is shown deforming the blockage in order to restore the patency of the vessel 100 although, as described above, other devices and methods may be used to capture, deform, or break up the blockage 15.

The electrodes may be disposed in various locations in the coronary arterial system. For example, as shown in FIGS. 3 and 4A-4C, the electrodes 28, 30, 38, 116, 117 disposed along the guide catheter 22, along the guidewire 24 and/or along the therapeutic system 110 proximal of the blockage 15 are disposed in the coronary arterial system between the ostium 11 and the blockage 15.

In other embodiments, the MI treatment system may include a second guidewire or lead (not shown). The second guidewire or lead may be disposed in the coronary arterial system, for example through the guide catheter 22. The second guidewire or lead may be extended into a different portion of the coronary arterial system, for example a branch vessel of the coronary arterial system other than the branch in which the blockage 15 is disposed. Examples are provided in U.S. patent application No. 12/422,770, entitled "Hemostasis Valve and Guidewire Pacing System", and filed Apr. 13, 2009, which is herein incorporated by reference in its entirety for all purposes.

Further, the MI treatment system may also comprise an additional guidewire or lead that can be separately advanced through the patient's vasculature to other portions of the heart such as the right atrium, the right ventricle, or into the coronary venous system via the coronary sinus. In other embodiments, the MI treatment system may comprise an epicardial lead that is configured to stimulate the heart from the epicardial surface. These alternate or additional guidewires or leads provide alternate locations to deliver cardioprotective pacing.

The multiple electrodes disposed on the MI treatment system provide multiple locations for stimulating the myocardial tissue of the heart. As generally described above, the MI treatment system is operatively coupled to a controller and the controller is adapted to send pacing signals to a target electrode. In addition, the controller may also be adapted to receive data representing a physiological parameter of the heart, for example the QRS interval, pulse pressure, systolic pressure, MAP, or another physiological parameters of interest. In general, the physiological parameter of interest represents, or is affected by, the level of synchrony between the right and left portions of the heart. For example, the QRS interval corresponds to the interval of time required to depolarize the ventricles of the heart, and is normally between 80 and 120 msec in duration. A QRS interval of longer than 120 msec is considered to represent dyssynchrony of the heart. In addition, this dyssynchrony may lead to inefficiencies in the heart and a lowering of the pulse pressure, the systolic pressure and/or the MAP.

The controller may be adapted to receive data representing the physiological parameter of interest prior to treating the MI. In some embodiments, the MI treatment system may be placed in the patient's vasculature and, prior to treating the MI, data representative of the physiological parameter is received by the controller from the MI treatment system or another device. If the physiological data is supplied from another device such as an EKG or sphygmomanometer, the other device may be operatively coupled to the controller or an operator may observe the data from the other device and manually input it into the controller.

In embodiments in which the physiological parameter is received by the controller prior to treating the MI, the controller may calculate a baseline value for the physiological parameter. For example, the baseline parameter may be calculated using data from a 1 minute, 5 minute, 10 minute, 30 minute, or one hour time interval prior to (e.g., immediately prior to) treating the MI. In other embodiments, the baseline parameter may be a preprogrammed value, or the baseline parameter may be manually entered, either based on data received from another device or based on the knowledge of a person performing the procedure. The preprogrammed or manually entered value may be between 80-140 msec, between 100-120 msec, about 120 msec or about 140 msec where the parameter is the QRS interval. When the physiological parameter is systolic blood pressure, the preprogrammed or manually entered value may be between 60-100 mmHg or between 70-90 mmHg, or about 80 mmHg, about 90 mmHg, or about 100 mmHg.

The controller is further adapted to send one or more test pacing signals to the various electrodes and, after optionally ensuring capture of the heart by the pacing signal, the physiological parameter is monitored when the heart is stimulated with each electrode. This process may be separately performed for two or more of the electrodes and the controller is adapted to compare the resulting physiological data from each of the electrodes.

In embodiments in which the physiological parameter is the QRS interval, the controller may be adapted to determine a target electrode that provides the greatest increase over the baseline data and use this electrode for cardioprotective pacing. In other embodiments in which a pressure is being used as the physiological parameter, the controller may be adapted to determine a target electrode that provides the greatest decrease in pressure over the baseline data and use this electrode for cardioprotective pacing.

In other embodiments, the controller has a preprogrammed or manually entered limit for the physiological parameter and the controller is adapted to use the first electrode that results in data that exceeds (for the QRS interval) or is lower than (for the pressure data) the limit. In yet other embodiments, the controller tests a number of electrodes and is adapted to use the electrode that results in data that exceeds (for the QRS interval), or is lower than (for the pressure data), the limit by the greatest amount. In embodiments in which the physiological parameter is the QRS interval, the lower limit may be about 110 msec, about 120 msec, about 130 msec, or about 140 msec. In embodiments in which systolic blood pressure is used, the drop in blood pressure may be at least about 10 mmHg, about 15 mmHg or about 20 mmHg.

In yet other embodiments, the controller is adapted to use the electrode that results in the widest (for the QRS interval) or the lowest (for pressure data) value, regardless of whether a baseline or limit value is provided.

In some embodiments, the controller may be adapted to provide a safety feature that shows or sounds an alarm when the dyssynchrony reaches a preprogrammed or manually entered level. For example, when the physiological parameter is the QRS interval, a maximum QRS interval may be about 170 msec, about 180 msec or about 190 msec or a certain percent increase (e.g., 100%) over the intrinsic QRS interval. When the physiological parameter is a blood pressure, a maximum drop in the pressure may be about 25 mmHg, about 35 mmHg or a certain percentage decrease (e.g., 25% or 30%) relative to the blood pressure baseline. In some embodiments, an operator may be provided an opportunity to discontinue the treatment in response to the alarm or the system may automatically discontinue the treatment in response to the alarm. In other embodiments, the controller is adapted such that it will not use the electrodes that have physiological parameter over (when QRS is being used) or under (when blood pressures are being used) a preprogrammed or manually entered limit, or, if all of the electrodes are outside these limits, the controller may be adapted to use the electrode that is outside these limits the least amount. In addition, in some embodiments the controller is adapted to alarm if the physiological parameter does not return to an acceptable level after the cardioprotective pacing is discontinued. For example, the controller may provide an alarm if the QRS interval does not return to within 110% or 120% of the baseline QRS interval, or return to below 120 msec. As another example, the controller may provide an alarm if the pressure does not return to within 10 mmHg, to within 15 mmHg, or to greater than 60 mmHg or greater than 70 mmHg.

In addition, the controller may also be adapted to intermittently test different electrodes when providing cardioprotective pacing to determine a target electrode with the most desirable physiological parameter. In this manner, if the physiological parameter at different sites changes over time (e.g., if the reperfusion causes a change in the physiological parameter at different locations or if one or more electrodes changes position during the procedure), the controller may be adapted to change the target electrode to which it is sending the pacing signal.

In some embodiments, the controller is also adapted to control the operation of the therapeutic device 110, for example the inflation of the balloon 114 shown in FIGS. 4A-4C. Once the therapeutic device 110 is in place in the blockage 15, an operator of the MI treatment system indicates to the controller that the therapeutic device 110 is in place. The controller is then adapted to operate the therapeutic device 110. In addition, in some embodiments the controller is automated to provide cardioprotective pacing from the desired electrode, and the pacing may be provided before, during and/or after the therapy is provided from the therapeutic device 110. (Providing therapy "contemporaneously" with opening the blockage generally includes immediately before, during, or immediately after opening the blockage.) In other embodiments, an operator determines when he cardioprotective pacing is delivered by the controller, for example before, during and/or after the therapy is provided from the therapeutic device 110.

Figure 5:
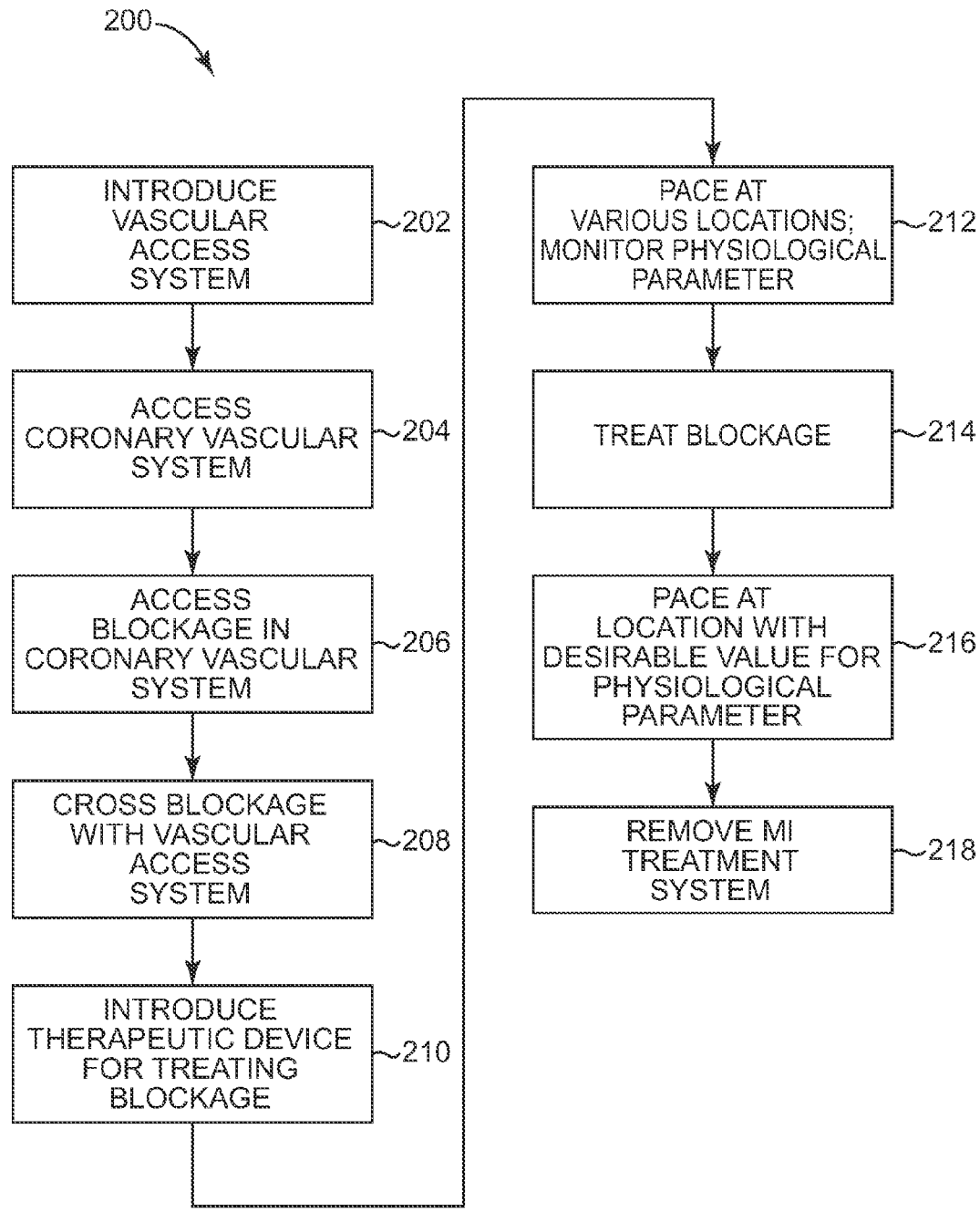
FIG. 5 shows a flow chart of a method of treating MI according to some embodiments of the present invention.

FIG. 5 shows a flow chart of a method 200 of treating MI according to some embodiments of the present invention. A vascular access system is introduced to a patient's vascular system (block 202). As one example, the vascular access system may be any of the vascular access systems described above and may be introduced by accessing the femoral artery.

The vascular access system is then used to gain access to the coronary vascular system (block 204). For example, the vascular access system is advanced through the patient's vasculature, into the aorta and into the coronary arterial system as described above. In embodiments in which the vascular access system includes both a guide catheter and a guidewire, the guide catheter may be advanced through the vasculature first. Once the guide catheter has accessed the vasculature of interest (e.g., the ostium 11), the guidewire may be advanced through the guide catheter and into the vasculature of interest. The guidewire may then be used to sub-select a desired branch of the vasculature (e.g., the coronary vasculature), for example to approach a blockage in the coronary vasculature (block 206).

Once access is obtained to the blockage in the coronary vasculature, the guidewire is used to cross the blockage (block 208), thus providing a guide for a therapeutic device to be advanced into the blockage. The therapeutic device for treating the blockage is then introduced to the patient's vasculature and advanced along the guidewire into the blockage (block 210).

As described above, the MI treatment system may then send one or more test pacing signals to various electrodes in order to determine the site at which the physiological parameter (e.g., any of the physiological parameters discussed above) has a desired value (e.g., any of the desired values or value ranges discussed above) (block 212).

The blockage is then treated (block 214) with the therapeutic device, for example as described above. After treatment is complete (e.g., immediately after treatment is complete), cardioprotective pacing is provided via the target electrode that is determined in block 212. In other embodiments, the cardioprotective pacing may be provided before, during, and/or after the cardioprotective pacing is provided.

In embodiments in which baseline data for the physiological parameter is collected or manually entered, the baseline data may be collected or entered prior to introducing the vascular access system (prior to block 202). The baseline data may also be collected using electrodes or other sensors disposed on the vascular access system and, as such, the baseline data is collected after block 202. Further, the baseline data may also be collected using the therapeutic device and, as such, the baseline data is collected after block 210. Also, in embodiments in which a second guidewire or lead is used to provide alternate or additional points of stimulation, the second guidewire or lead may be introduced prior to introducing the vascular access system (prior to block 202), it may be introduced through the vascular access system after block 202, or it may be introduced separately from the vascular access system at any time before or during the procedure 200.

Figure 6:
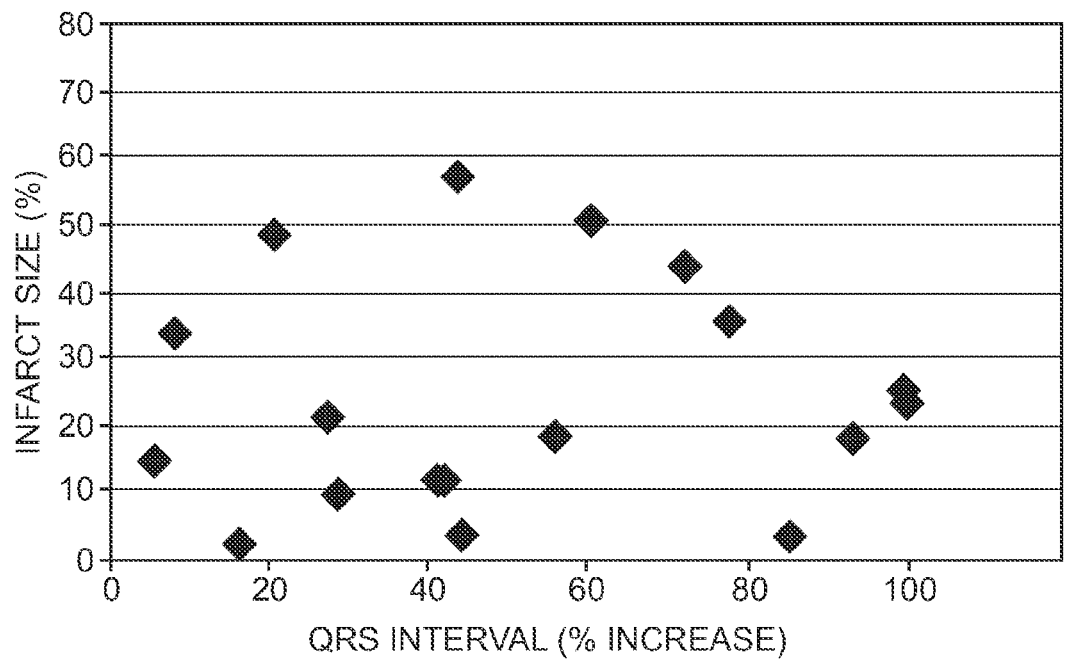
FIG. 6 shows a chart of the infarct size versus the increase in QRS complex or interval for pigs.

FIG. 6 shows a graph of the size of the infarct zone with respect to the QRS interval that was observed when providing cardioprotective pacing in pigs during a simulated MI. The infarct zone data is calculated by first determining the total area of the heart that would theoretically be affected by the blockage. The area that is actually affected by the blockage is then determined, and this area is divided by the area that would theoretically be affected by the blockage. This fraction (shown as a percentage in FIG. 6) is then plotted against the QRS data. The QRS data that is used in FIG. 6 is a percentage increase over a baseline QRS interval. This data indicates that there is at least some correlation between a greater increase in the QRS interval (and, therefore, a greater dyssynchrony) and the reduction of the infarct size.

Figure 7:
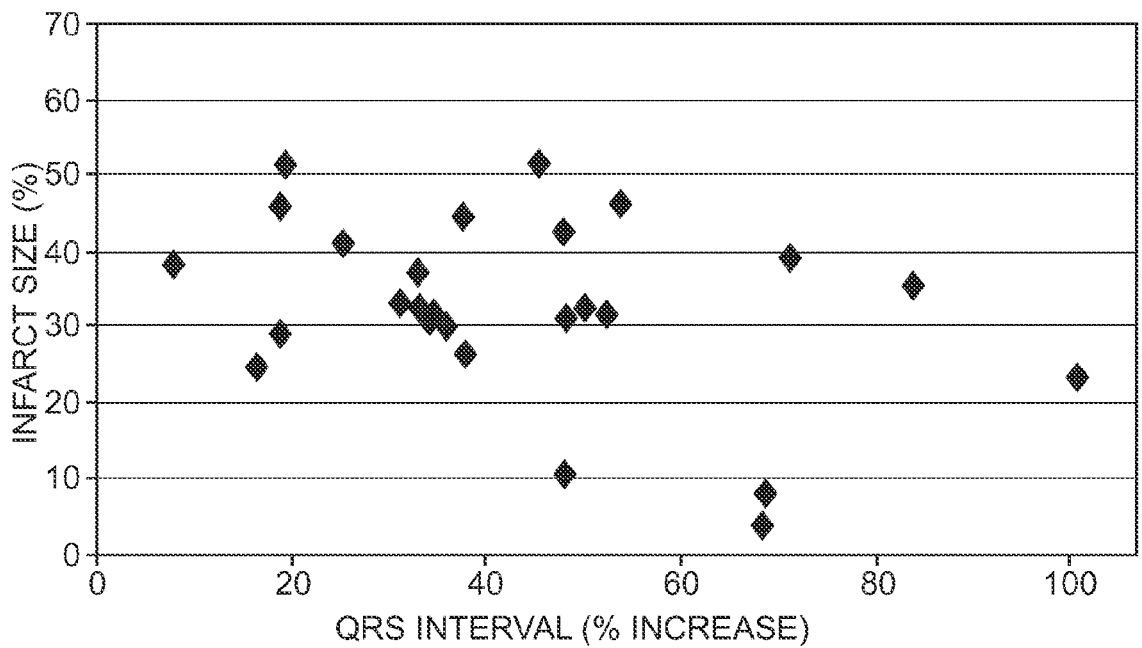
FIG. 7 shows a chart of the infarct size versus the increase in QRS complex or interval for humans.

In addition, FIG. 7 shows similar data that was collected during a human study. The humans presented with, and were treated for, MI, and cardioprotective pacing was provided during the treatment. Again, the data indicates that there is at least some correlation between a greater increase in the QRS interval (and, therefore, a greater dyssynchrony) and the reduction of the infarct size.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method of treating a heart having a myocardial infarction, the heart including a coronary vascular system with a blockage in a portion of the coronary vascular system, the method including:
   introducing one or more devices into the coronary vascular system, the one or more devices having a total of two or more electrodes disposed thereon;
   disposing the electrodes in at least two different locations in the coronary vascular system;
   pacing the heart from one of the electrodes and subsequently from another of the electrodes;
   monitoring a physiological parameter that represents the level of synchrony of the heart when individually pacing from each of the electrodes;
   determining a target electrode that provides the highest level of dyssynchrony; and
   temporarily pacing from the target electrode to increase dyssynchrony contemporaneously with treatment of the blockage and reperfusing blood flow to the myocardial infarction.

2. The method of claim 1, wherein the one or more devices includes a guide catheter, a guidewire, and a therapeutic device for opening a blockage in a vessel.

3. The method of claim 1, wherein one of the electrodes is disposed at a location distal of the blockage and another of the electrodes is disposed at a location proximal of the blockage.

4. The method of claim 1, wherein at least one of the electrodes is disposed in a vessel other than the vessel containing the blockage.

5. The method of claim 4, wherein at least one of the electrodes is disposed in the coronary venous system.

6. The method of claim 1, wherein the physiological parameter resulting from a pacing signal sent to the target primary electrode is a QRS interval of at least 120 msec.

7. The method of claim 1, wherein the temporary pacing is provided after opening the blockage.

8. The method of claim 1, wherein the physiological parameter is one of pulse pressure, systolic pressure or MAP.

* * * * *